United States Patent
Sullivan et al.

(10) Patent No.: US 9,693,765 B2
(45) Date of Patent: Jul. 4, 2017

(54) SURGICAL ASSEMBLY FOR ROTATOR CUFF REPAIR

(71) Applicant: Arthrex, Inc., Naples, FL (US)

(72) Inventors: Derek C. Sullivan, Naples, FL (US); Peter J. Dreyfuss, Naples, FL (US); Laurence D. Higgins, Brookline, MA (US)

(73) Assignee: Arthrex, Inc., Naples, FL (US)

( * ) Notice: Subject to any disclaimer, the term of this patent is extended or adjusted under 35 U.S.C. 154(b) by 247 days.

(21) Appl. No.: 14/606,711

(22) Filed: Jan. 27, 2015

(65) Prior Publication Data

US 2015/0297211 A1    Oct. 22, 2015

Related U.S. Application Data

(60) Provisional application No. 61/931,967, filed on Jan. 27, 2014.

(51) Int. Cl.
*A61B 17/04* (2006.01)
*A61B 17/84* (2006.01)
(Continued)

(52) U.S. Cl.
CPC ........ *A61B 17/0401* (2013.01); *A61B 17/842* (2013.01); *A61B 17/1778* (2016.11); *A61B 2017/0475* (2013.01); *A61F 2/40* (2013.01)

(58) Field of Classification Search
CPC .............. A61B 17/0401; A61B 17/842; A61B 2017/0475; A61B 2017/0459;
(Continued)

(56) References Cited

U.S. PATENT DOCUMENTS

| | | | |
|---|---|---|---|
| 5,891,168 A * | 4/1999 | Thal | A61B 17/0401 606/139 |
| 6,514,274 B1 * | 2/2003 | Boucher | A61B 17/0401 606/232 |

(Continued)

FOREIGN PATENT DOCUMENTS

| EP | 1 568 326 A1 | 8/2005 |
|---|---|---|
| EP | 2 601 894 A1 | 6/2013 |

*Primary Examiner* — Todd J Scherbel
*Assistant Examiner* — Son Dang
(74) *Attorney, Agent, or Firm* — Blank Rome LLP

(57) ABSTRACT

Knotless, adjustable anchor systems that allow for knotless tensioning of tissue (such as the rotator cuff) after anchor implantation. The knotless, adjustable anchor system includes knotless anchors (for example, swivel and/or screw-in suture anchors and/or push-in suture anchors) that are modified to carry a self-locking, adjustable construct (for example, a suture assembly with a spliced suture loop) and to position the self-locking, adjustable construct at the repair site. The system allows for knotless tensioning of the tissue after the knotless anchors have been implanted. The medial row anchors are implanted and passed through tissue in a similar fashion as the current Corkscrew® or SwiveLock® C anchors are. The lateral row anchors are similar to a knotless SutureTak® but modified to accommodate a larger suture to hold a larger load. The suture is interconnected to the medial row and returned back to the lateral row for loading into the splice.

15 Claims, 12 Drawing Sheets

(51) Int. Cl.
*A61F 2/40* (2006.01)
*A61B 17/17* (2006.01)

(58) Field of Classification Search
CPC .... A61B 2017/1778; A61B 2017/0464; A61B 2017/0414; A61F 2/40
See application file for complete search history.

(56) References Cited

U.S. PATENT DOCUMENTS

| | | | |
|---|---|---|---|
| 6,716,234 B2 | 4/2004 | Grafton et al. | |
| 7,329,272 B2 | 2/2008 | Burkhart et al. | |
| 7,390,332 B2* | 6/2008 | Selvitelli | A61B 17/0401 606/144 |
| 7,803,173 B2 | 9/2010 | Burkhart et al. | |
| 7,892,256 B2 | 2/2011 | Grafton et al. | |
| 7,981,140 B2 | 7/2011 | Burkhart | |
| 8,231,653 B2* | 7/2012 | Dreyfuss | A61B 17/0401 606/232 |
| 8,419,794 B2 | 4/2013 | ElAttrache et al. | |
| 8,545,535 B2* | 10/2013 | Hirotsuka | A61B 17/0401 606/232 |
| 8,672,968 B2* | 3/2014 | Stone | A61B 17/0401 606/228 |
| 2007/0083236 A1* | 4/2007 | Sikora | A61B 17/0401 606/232 |
| 2007/0135843 A1* | 6/2007 | Burkhart | A61B 17/0401 606/232 |
| 2008/0004659 A1 | 1/2008 | Burkhart et al. | |
| 2008/0255613 A1 | 10/2008 | Kaiser et al. | |
| 2008/0262544 A1* | 10/2008 | Burkhart | A61B 17/0401 606/232 |
| 2009/0054928 A1* | 2/2009 | Denham | A61B 17/0401 606/232 |
| 2009/0082805 A1* | 3/2009 | Kaiser | A61B 17/0401 606/228 |
| 2009/0318961 A1* | 12/2009 | Stone | A61B 17/0401 606/228 |
| 2010/0249834 A1* | 9/2010 | Dreyfuss | A61B 17/0401 606/232 |
| 2012/0123473 A1* | 5/2012 | Hernandez | A61B 17/0401 606/232 |
| 2012/0265219 A1* | 10/2012 | Rushdy | A61B 17/0401 606/139 |
| 2013/0023928 A1* | 1/2013 | Dreyfuss | A61B 17/0401 606/228 |
| 2013/0096611 A1* | 4/2013 | Sullivan | A61B 17/0485 606/232 |
| 2013/0165972 A1 | 6/2013 | Sullivan | |
| 2013/0345750 A1 | 12/2013 | Sullivan | |
| 2014/0081323 A1* | 3/2014 | Hawkins | A61B 17/0401 606/232 |
| 2014/0249577 A1* | 9/2014 | Pilgeram | A61B 17/0485 606/228 |

\* cited by examiner

SURGICAL ASSEMBLY FOR ROTATOR CUFF REPAIR

CROSS-REFERENCE TO RELATED APPLICATIONS

This application claims the benefit of U.S. Provisional Application No. 61/931,967, filed Jan. 27, 2014, the entire disclosure of which is incorporated by reference herein.

FIELD OF THE INVENTION

The present invention relates to methods and instruments for fixation of sutures and tissue to bone.

BACKGROUND OF THE INVENTION

Reattachment of soft tissue to bone employing knotless fixation devices are known in the art, particularly for the formation of double row constructs in arthroscopic rotator cuff repairs. For example, the SpeedBridge™ double row technique, developed by Arthrex, Inc., uses threaded swivel anchors (such as disclosed in U.S. Patent Publication No. 2008/0004659, the disclosure of which is herein incorporated by reference in its entirety) combined with FiberTape® to create a quick and secure SutureBridge™ construct, such as disclosed in U.S. Pat. No. 8,419,794 (herein incorporated by reference) with no knots and only two suture passing steps.

In the SpeedBridge™ technique, a swivel anchor, preferably an Arthrex 4.75 mm SwiveLock® C, loaded with one strand of FiberTape®, is inserted into a medial bone socket. A FiberLink™ and Scorpion™ is used to shuttle both FiberTape® tails through the rotator cuff simultaneously. Next, one FiberTape® tail from each medial anchor is retrieved and loaded through the SwiveLock® C eyelet. The loaded eyelet is inserted into a prepared lateral bone socket until the anchor body contacts bone, and the tension is adjusted if necessary. The SwiveLock® C driver is rotated in a clockwise direction to complete the insertion. Using an open ended FiberWire® cutter, the FiberTape® tails are cut, one and a time, to complete the technique.

In the above-described SpeedBridge™ technique, it can be difficult to tension the sutures or the FiberTape® tails through the rotator cuff, except by deeper insertion of lateral anchors. Accordingly, there is a need for a multi-anchor tissue repair without the need for tying knots but still with the ability to tension the tissue properly, especially after implantation of the anchors. Also needed is an improved technology for knotless fixation of the rotator cuff with easier suture management and increased tensioning of the rotator cuff.

SUMMARY OF THE INVENTION

The instruments and methods of the present invention provide knotless, adjustable anchor systems that allow for knotless tensioning of tissue (such as the rotator cuff) after anchor implantation. The knotless, adjustable anchor system includes knotless anchors (for example, swivel and/or screw-in suture anchors and/or push-in suture anchors) that are modified to carry a self-locking, adjustable construct (for example, a suture assembly with a spliced suture loop) and to position the self-locking, adjustable construct at the repair site. The system allows for knotless tensioning of the tissue after the knotless anchors have been implanted.

The reconstruction system of the present invention is similar to the SpeedBridge™ construct in that it also has a two-row knotless rotator cuff repair. The main difference, however, is that the tension can be adjusted after the anchors have been implanted. The medial row anchors are implanted and passed through tissue in a similar fashion as the current Corkscrew® or SwiveLock® C anchors are. The lateral row anchors are similar to a knotless SutureTak® but modified to accommodate a larger suture to hold a larger load. The suture would be interconnected to the medial row and returned back to the lateral row for loading into the splice.

Other features and advantages of the present invention will become apparent from the following description of exemplary embodiments of the invention described with reference to the accompanying drawings.

DETAILED DESCRIPTION OF THE PREFERRED EMBODIMENTS

Figure 1:
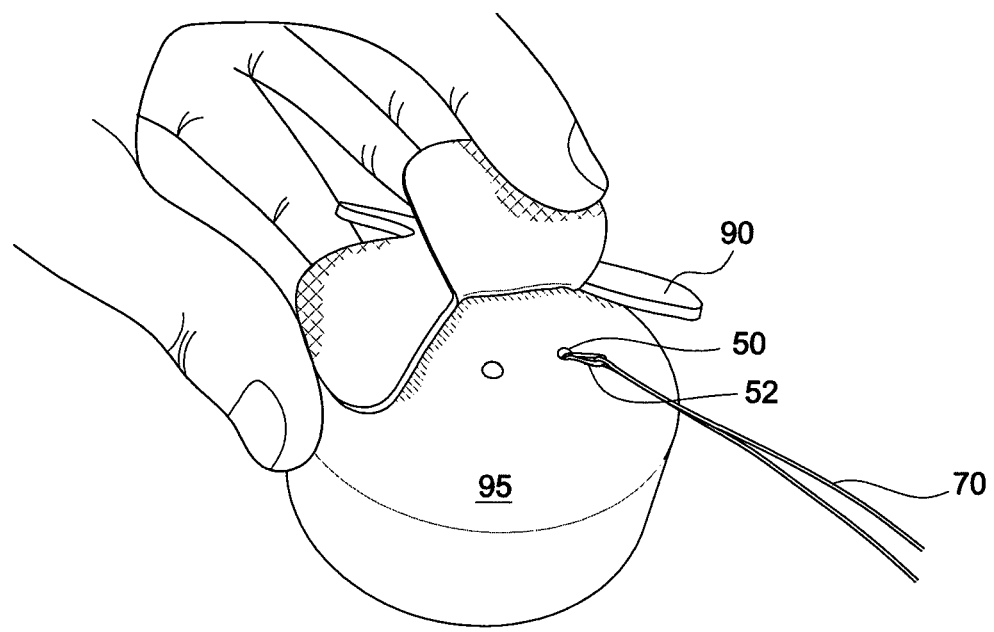
FIGS. 1-21 illustrate exemplary steps of a method of rotator cuff repair with an adjustable, knotless, tensionable system and according to an exemplary embodiment of the present invention.

The present invention provides surgical constructs, systems and techniques for knotless soft tissue repair and fixation, such as fixation of soft tissue (ligament, tendon, graft, etc.) to bone, and for the tensioning of the tissue (for example, rotator cuff) after anchor implantation.

The knotless systems of the present invention use lateral anchors that employ a mechanism similar to that of a knotless SutureTak® but provide improvements in the design of the tensioning construct. The knotless lateral anchors are modified to accommodate a larger suture to hold a larger load. The suture would be interconnected to the medial row and returned back to the lateral row for loading into the splice. Details of the formation of an exemplary knotless lateral suture anchor employed in the embodiments of the present invention and with a splice-forming mechanism are set forth in U.S. Patent Publication No. 2013/0345750 entitled "Tensionable Knotless Labral Anchor and Methods of Tissue Repair," U.S. Patent Publication No. 2013/0096611 entitled "Tensionable Knotless Anchors with Splice and Methods of Tissue Repair," and U.S. Patent Publication No. 2013/0165972 entitled "Tensionable Knotless Anchor Systems and Methods of Tissue Repair," the disclosures of all of which are incorporated by reference in their entirety herein.

As detailed below, the present invention provides knotless suture constructs with various designs and methods of fixation of soft tissue to bone with the ability to tension/retension the suture constructs after their implantation. The knotless suture constructs have applicability to soft tissue repairs including labral, rotator cuff, Achilles tendon and biceps, among many others.

According to an exemplary embodiment, the invention provides a tissue repair system for attachment of tissue to bone, the system including at least one flexible strand extending between at least one medial knotless fixation device and at least one lateral knotless tensionable anchor (self-cinching knotless construct). The medial knotless fixation device may be a swivel anchor, a screw-in anchor or a push-in suture anchor (such as an Arthrex SwiveLock® anchor, disclosed in U.S. Patent Application Publication No. 2008/0004659 or a PushLock® anchor, disclosed in U.S. Pat. No. 7,329,272). The lateral anchor may be a Suture-Tak® anchor in the form of a knotless suture anchor with a splice-forming mechanism as set forth in U.S. Patent Publication No. 2013/0345750, entitled "Tensionable Knotless Labral Anchor and Methods of Tissue Repair," U.S. Patent Publication No. 2013/0096611, entitled "Tensionable Knotless Anchors with Splice and Methods of Tissue Repair" and U.S. Patent Publication No. 2013/0165972, entitled "Tensionable Knotless Anchor Systems and Methods of Tissue Repair," the disclosures of all of which are incorporated by reference in their entirety herein.

According to another exemplary embodiment, the tissue repair system for attachment of tissue to bone includes at least one flexible strand extending between a medial row of knotless fixation devices and a lateral row of the knotless tensionable anchors (self-cinching knotless constructs) that allow for knotless labral repair as well as tensioning after implantation of the medial anchors. The labrum can also be attached to the anchor site instead of alongside it. At least one (preferably all) of the medial row fixation devices is a swivel anchor, a screw-in anchor or a push-in suture anchor (such as an Arthrex SwiveLock®) anchor, disclosed in U.S. Patent Application Publication No. 2008/0004659 or a PushLock® anchor, disclosed in U.S. Pat. No. 7,329,272). At least one (preferably all) of the lateral anchors is a Suture-Tak® anchor, i.e., a knotless suture anchor with a splice-forming mechanism as set forth in U.S. Patent Publication No. 2013/0345750, entitled "Tensionable Knotless Labral Anchor and Methods of Tissue Repair," U.S. Patent Publication No. 2013/0096611, entitled "Tensionable Knotless Anchors with Splice and Methods of Tissue Repair" and U.S. Patent Publication No. 2013/0165972, entitled "Tensionable Knotless Anchor Systems and Methods of Tissue Repair," the disclosures of all of which are incorporated by reference in their entirety herein.

In an exemplary embodiment, the lateral knotless fixation device may be a self-cinching knotless construct which is pre-loaded with a tensionable construct formed of a flexible strand (suture) attached to a shuttling device (a shuttle/pull device or suture passing device for example, a FiberLink™ or a nitinol loop). The shuttling device is configured to be pulled out of the body of the fixation device (anchor) to allow the flexible strand to pass through itself and form a splice within the body of the fixation device (or outside of the body of the fixation device). The body of the fixation device is cannulated and the tensionable construct extends through the body of the fixation device. The body is provided with a proximal end that receives a tip of a driver and a distal end that is configured to house a knot of the flexible strand, so that the flexible strand has only one free end.

The present invention also provides methods of soft tissue repair which do not require tying of knots and allow adjustment of both the tension of the suture and the location of the tissue with respect to the bone. In the exemplary methods detailed below with reference to FIGS. 1-21, the lateral tensionable knotless anchors are used for labral knotless repairs which allow the labrum to attach to the anchor site and also for tensioning after the anchor implantation. The lateral tensionable knotless anchors detailed below may be provided with the splice-forming mechanism, or may be provided pre-loaded with the splice, i.e., with no shuttle/pull device attached to the suture (no shuttle/pull device necessary). The medial anchors and the lateral tensionable knotless anchors may be used to achieve simple stitch repairs, mattress stitch repairs or any other suturing repairs such as interlocked looped mattress repairs, among others.

As detailed below, the invention is similar in part to the SpeedBridge™ technique in that it has a two-row knotless rotator cuff repair. However, the present invention is different in that the tension can be adjusted after the lateral tensionable knotless anchors are implanted. The medial row anchors 50, 50a are implanted and passed through tissue 90 in a similar fashion as the current Corkscrew or SwiveLock anchors are. The lateral row tensionable knotless anchors 60, 60a are more similar to a knotless SutureTak®, but would accommodate a larger suture to hold a larger load. The suture would be interconnected to the medial row anchors 50, 50a and returned back to the lateral row tensionable knotless anchors 60, 60a for loading into the splice of the lateral row tensionable knotless anchors.

Referring now to the drawings, where like elements are designated by like reference numerals, FIGS. 1-21 illustrate exemplary steps of a method of soft tissue repair with an adjustable, knotless, tensionable system 100 of the present invention provided with exemplary-only first and second fixation devices 50, 50a, 60, 60a for knotless tensioning of soft tissue 90.

Figure 22A:
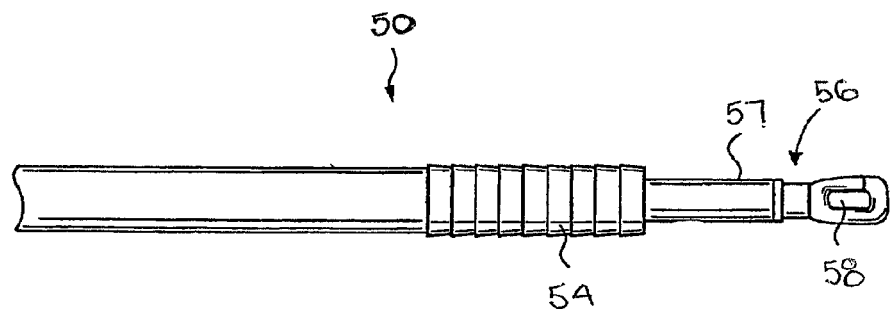
FIGS. 22A, 22B, and 23C illustrate exemplary anchors in accordance with the present invention.
Figure 22B:
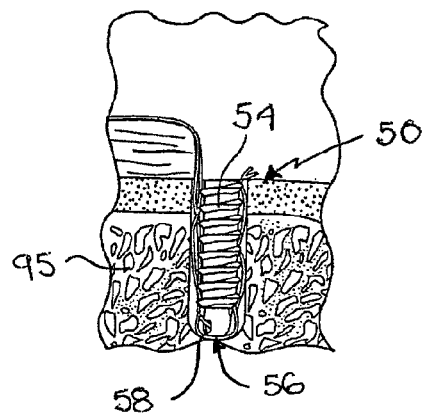

FIG. 1 (step 1)—Insert first medial row anchor 50 in bone 95. Attached is a suture shuttle 70, for example, a FiberLink® or nitinol wire loop. Suture shuttle 70 is attached to fixed loop 52 of the anchor 50. Anchor 50 is a fixation device in the form of any knotless anchor, for example, swivel and/or screw-in suture anchors and/or push-in suture anchors (such as an Arthrex SwiveLock® anchor, disclosed in U.S. Patent Application Publication No. 2008/0004659 or a PushLock®. anchor, disclosed in U.S. Pat. No. 7,329,272). Anchor 50 may include a cannulated fixation device 54 and a tip 56 that is rotatable and swivels with respect to cannulated fixation device 54, as seen in FIGS. 22A and 22B. Tip 56 may comprise, for example, a shaft 57 and an eyelet 58 at the end of shaft 57. The anchor 50, and its cannulated fixation device 54, may be, for example, a push-in anchor (FIG. 22A), as disclosed in U.S. Pat. No. 7,329,272, or a swivel anchor (FIG. 22B), as disclosed in U.S. Patent Application Publication No. 2008/0004659.

Figure 2:
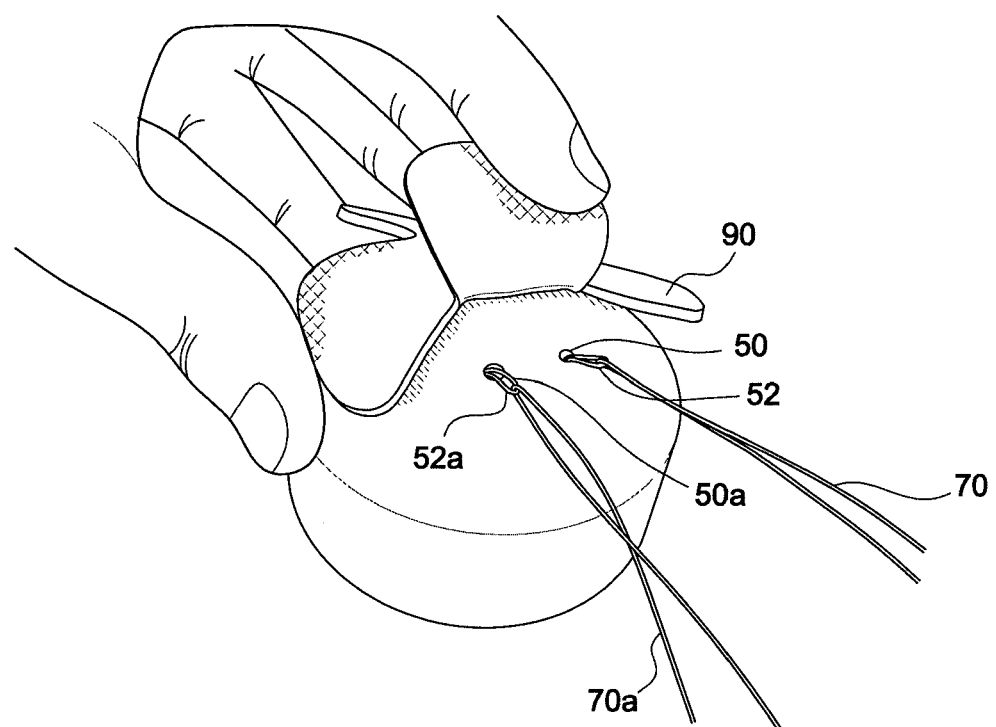

FIG. 2 (step 2)—Second medial row anchor 50a provided with attached suture shuttle 70a, for example, a FiberLink™ or nitinol wire loop, is inserted. Suture shuttle 70a is attached to a fixed loop 52a of the second medial row anchor 50a. Anchor 50a is also a fixation device in the form of any knotless anchor, for example, swivel and/or screw-in suture anchors and/or push-in suture anchors. (such as an Arthrex SwiveLock® anchor, disclosed in U.S. Patent Application Publication No. 2008/0004659 or a PushLock® anchor, disclosed in U.S. Pat. No. 7,329,272).

Figure 3:
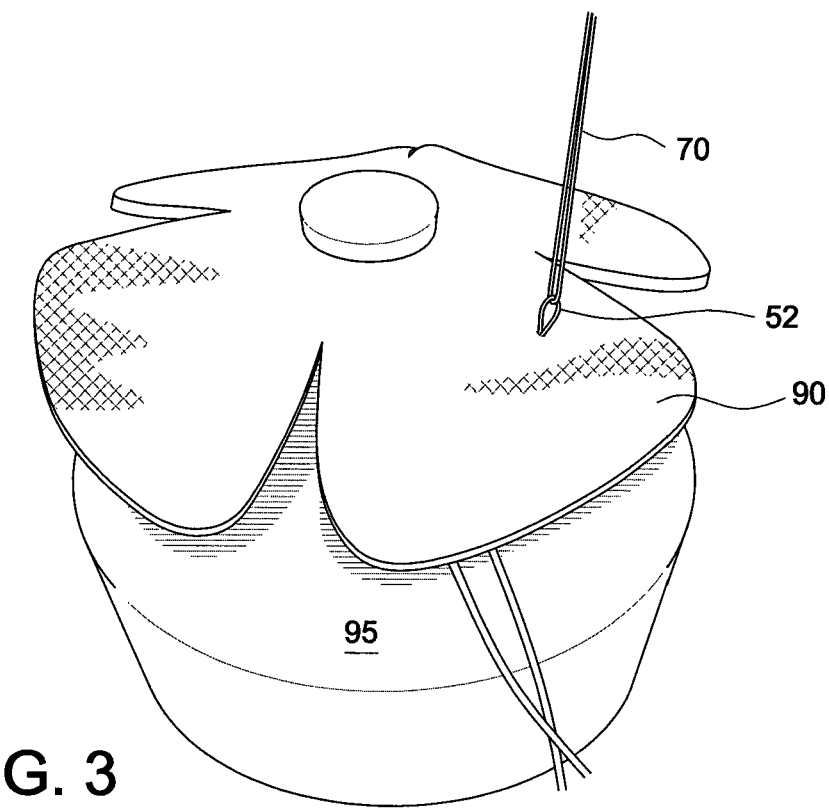

FIG. 3 (step 3)—Pass suture shuttle 70 through tissue 90 together with fixed loop 52.

Figure 4:
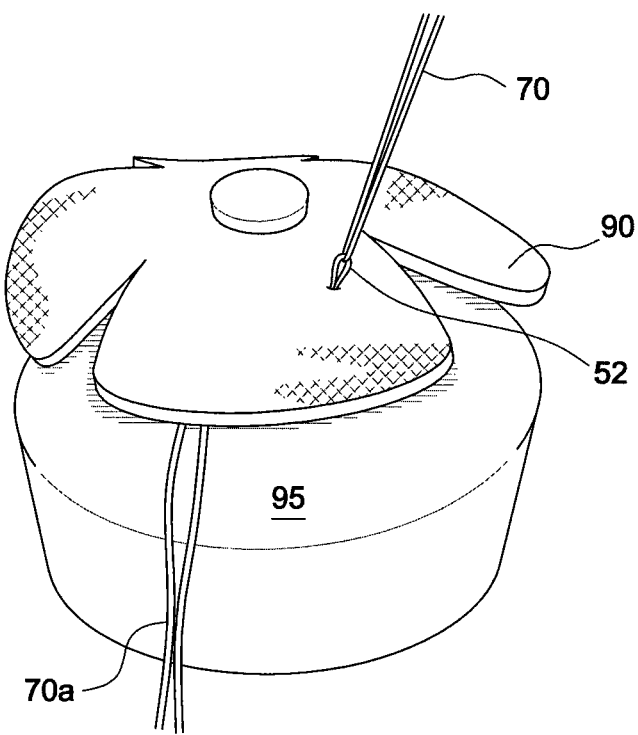

FIG. 4 (step 4)—same as step 3; fixed loop 52 exits tissue 90.

Figure 5:
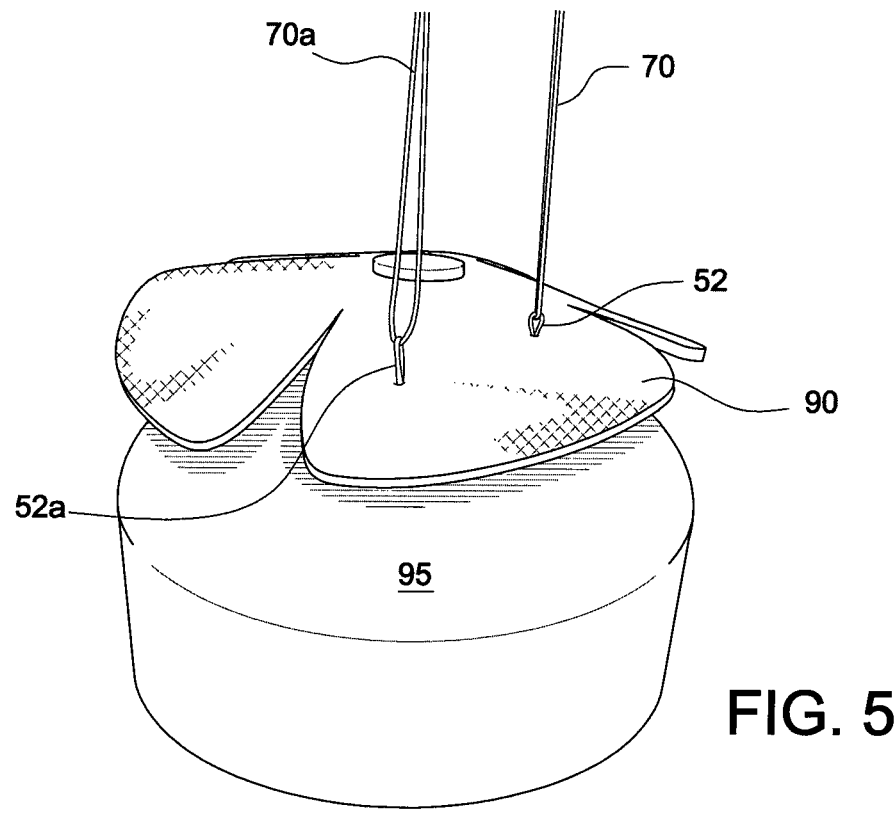

FIG. 5 (step 5)—Pass the suture shuttle 70a of the other anchor 50a in the same manner as the suture shuttle 70. Fixed loop 52a exits tissue 90 and rests on it.

Figure 6:
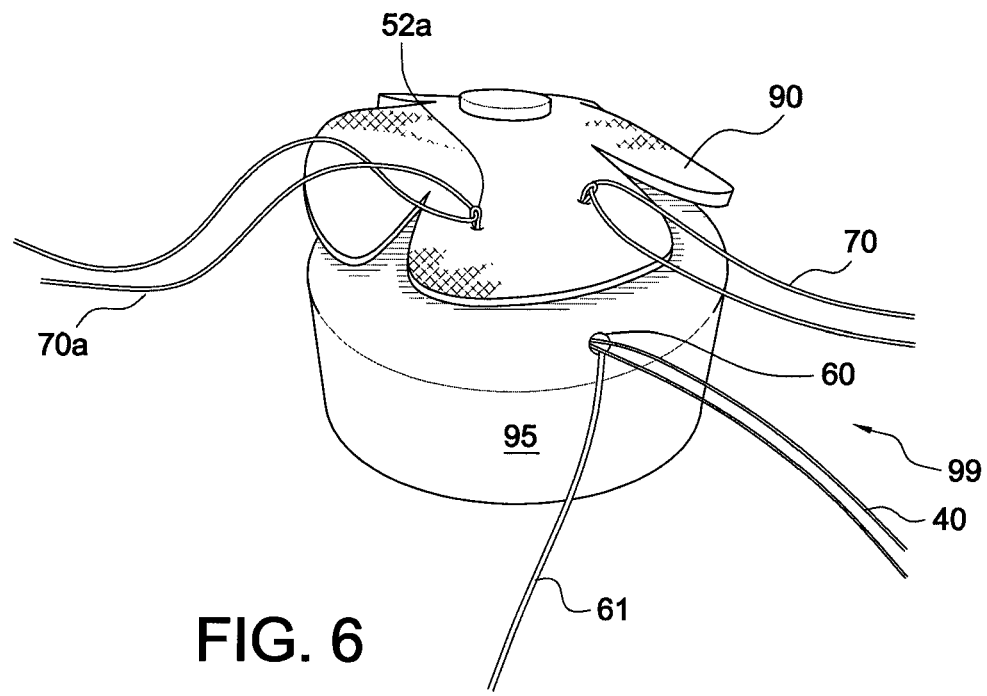

FIG. 6 (step 6)—Insert first lateral row anchor 60. This anchor has the same form and function as those of a knotless SutureTak® anchor, only it may be larger in diameter and suture size to accommodate a larger load. In an exemplary embodiment, the first lateral row anchor 60 is a self-cinching knotless construct which is pre-loaded with a tensionable construct 99 formed of suture 61 attached to a shuttling device 40 (shuttle/pull device 40 or suture passing device 40 in an exemplary form of a FiberLink™ or a nitinol loop/wire).

Figure 23:
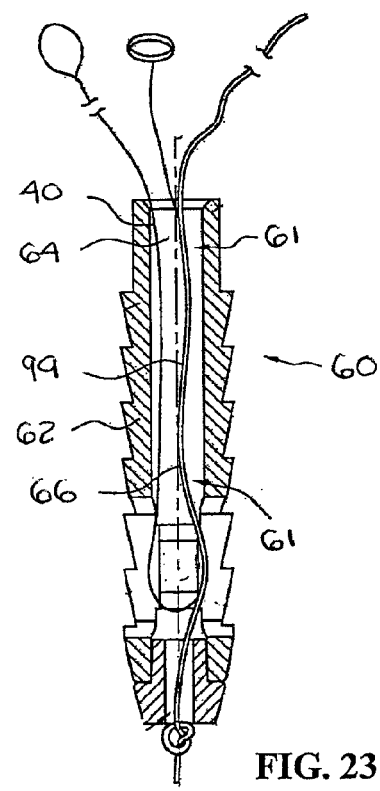

The first lateral row self-cinching knotless anchor 60 may be a fixation device that is inserted into a first bone tunnel and that comprises a body 62 with an inner bore 64 and a tensionable construct 99 pre-loaded on the fixation device, the tensionable construct consisting of a flexible strand 61 and a shuttling device 40 attached to the flexible strand, as seen in FIG. 23. In an exemplary embodiment, the shuttling device 40 resides within a second tunnel formed into bone, wherein the first tunnel is in communication with the second tunnel and wherein a diameter of the first tunnel is smaller than a diameter of the second tunnel.

The first lateral row self-cinching knotless anchor 60 may also comprise an anchor body, a flexible strand 61 extending through the body and a shuttling device 40 attached to the flexible strand, the flexible strand and the attached shuttling device being pre-loaded on the knotless anchor 60, the shuttling device being located outside or inside the body of the knotless anchor 60, so that when the flexible strand 61 is passed through, over or around tissue 90 to be fixated and through the shuttling device 40, a knotless closed loop having an adjustable perimeter and a splice are formed, as detailed below.

Figure 7:
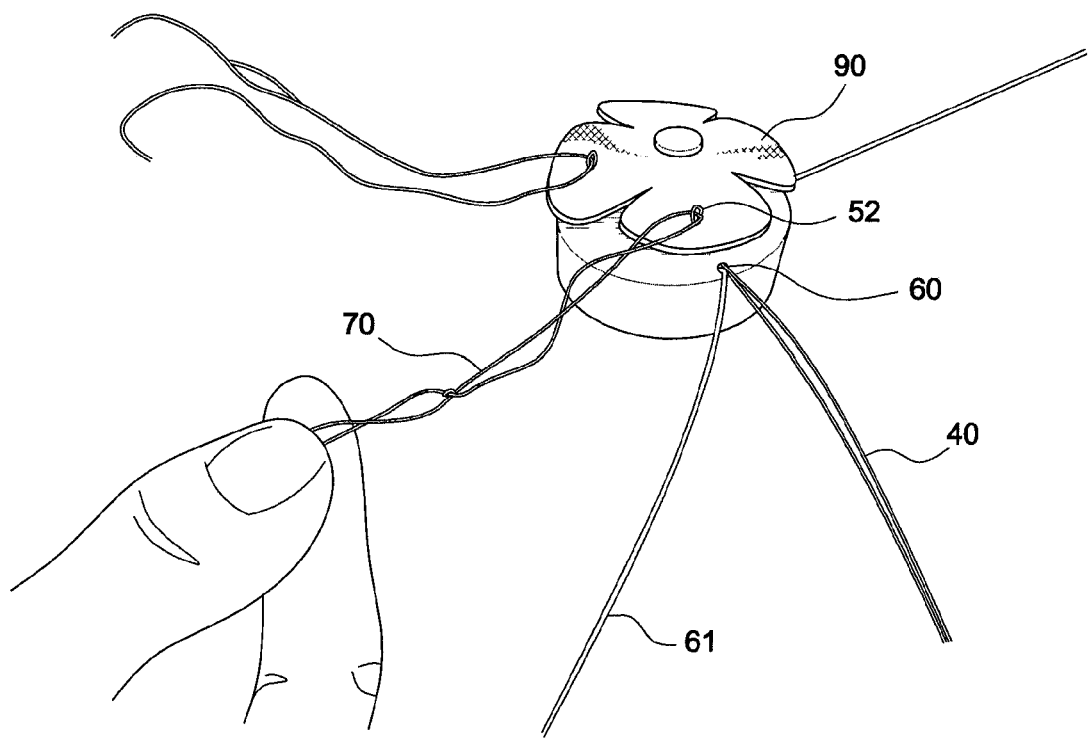

FIG. 7 (step 7)—Tether suture 61 from lateral row to suture shuttle from an anchor from the medial row. It could be either anchor depending on surgeon's preference.

Figure 8:
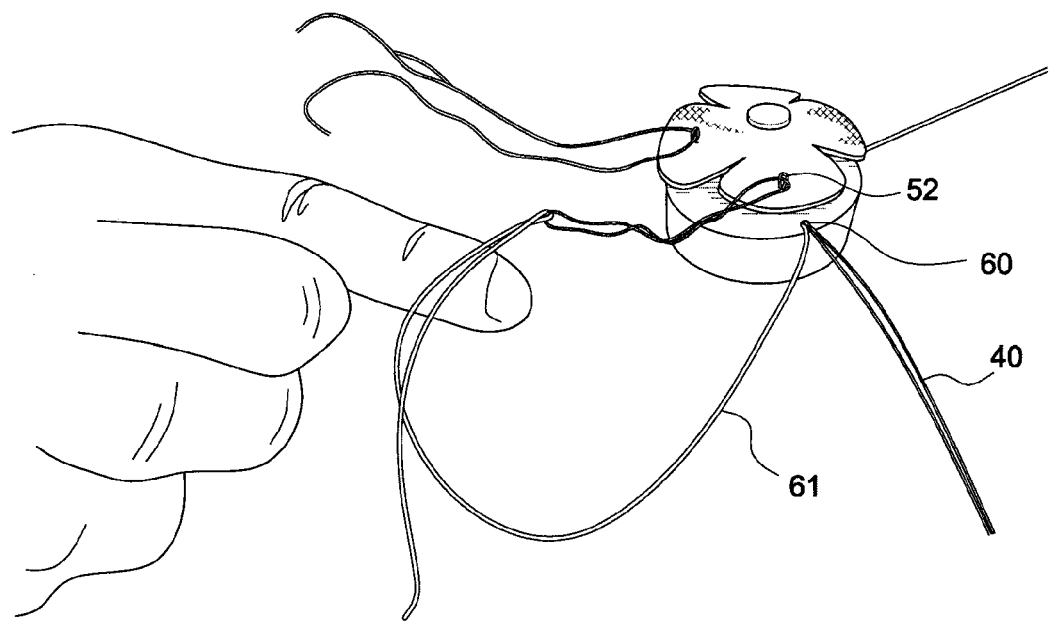

FIG. 8 (step 8)—Alternate view of step 7.

Figure 9:
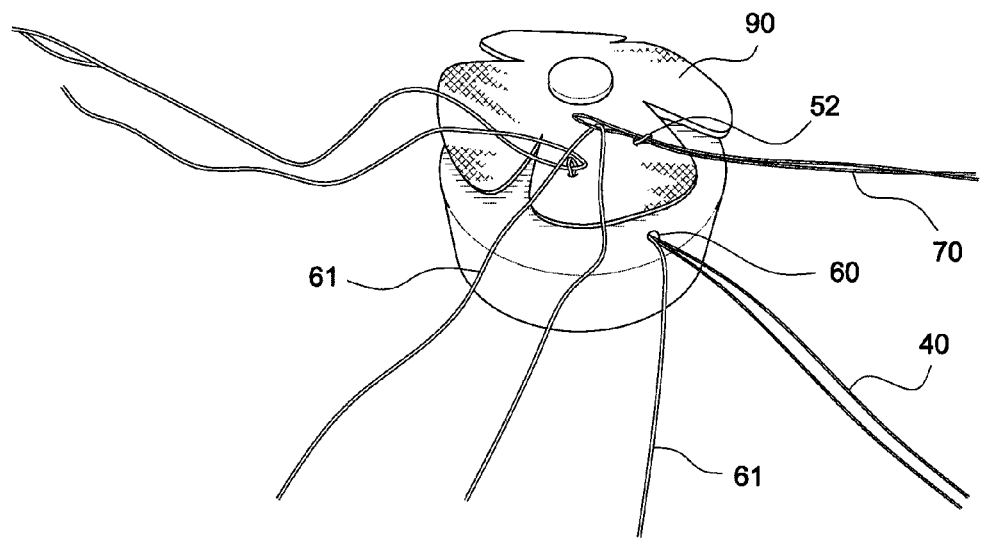

FIG. 9 (step 9)—Pull suture shuttle so the suture 61 from the knotless tensionable anchor 60 of the lateral row is pulled through the medial row anchor 50.

Figure 10:
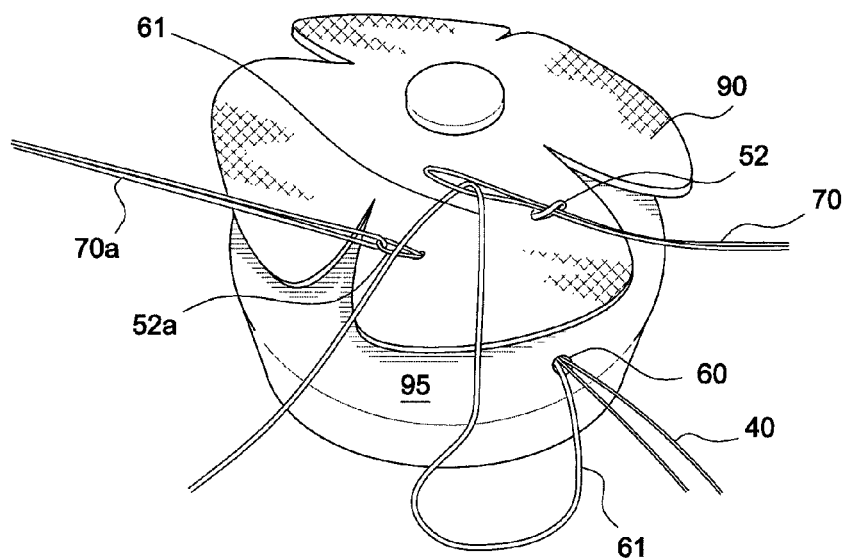

FIG. 10 (step 10)—close up view of step 9.

Figure 11:
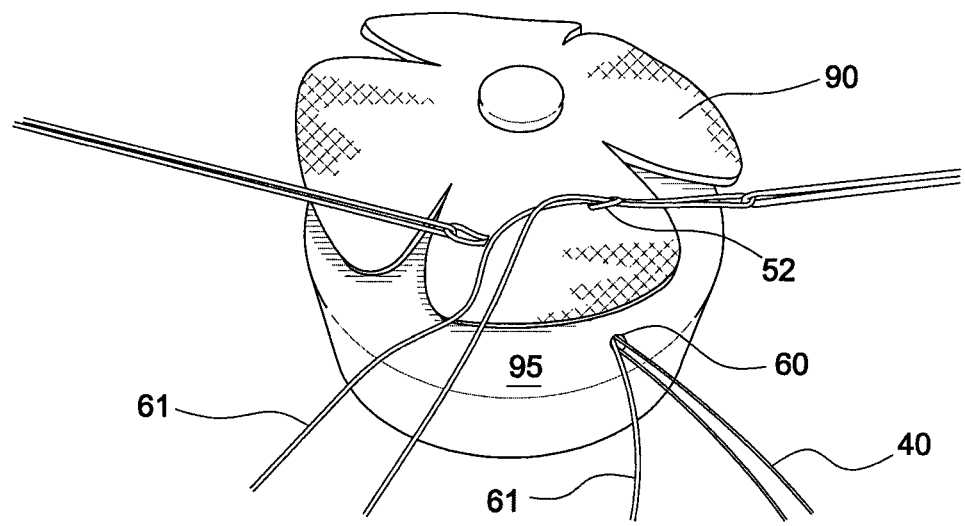

FIG. 11 (step 11)—Lateral row suture 61 being further pulled through the medial anchor 50.

Figure 12:
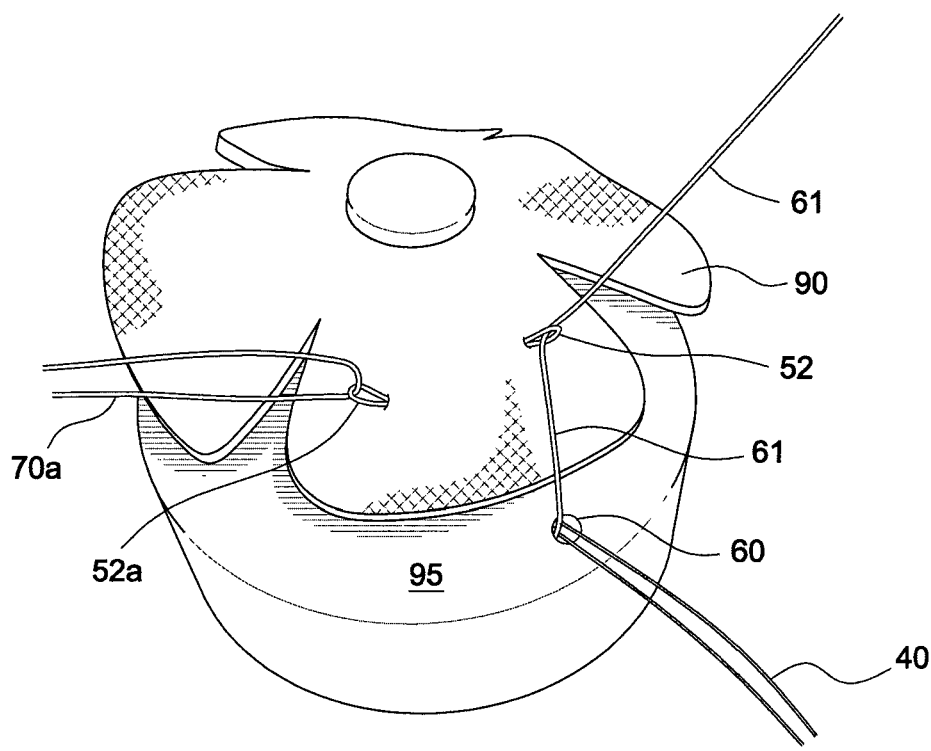

FIG. 12 (step 12)—Pull out the slack of the lateral row suture 61 and pull the strand out the same cannula as the nitinol wires.

Figure 13:
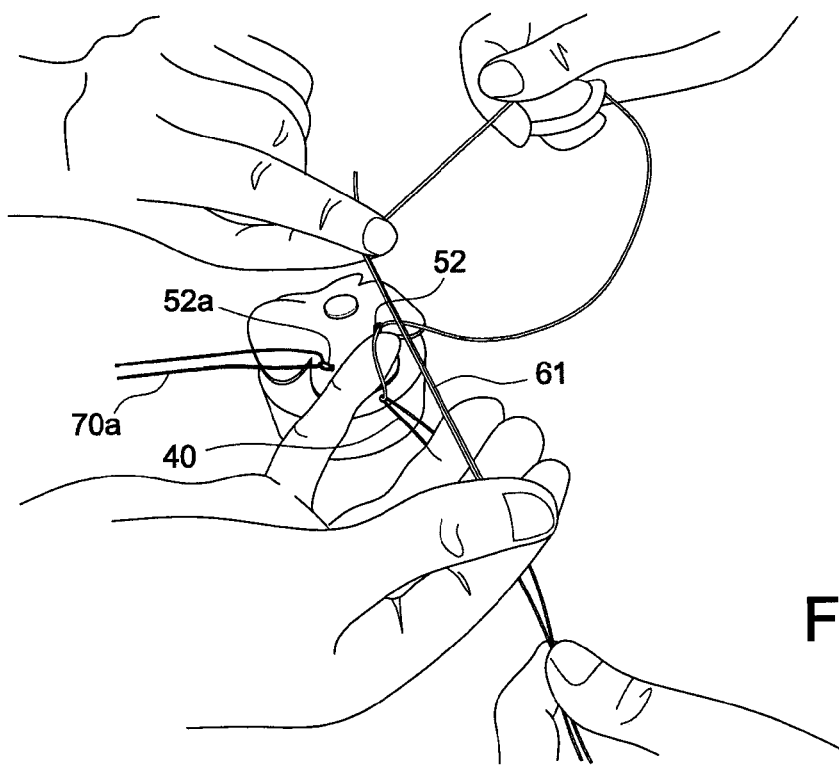

FIG. 13 (step 13)—Feed the tapered portion of the lateral row suture 61 through the open end of the shuttle/pull device 40 (nitinol wire 40).

Figure 14:
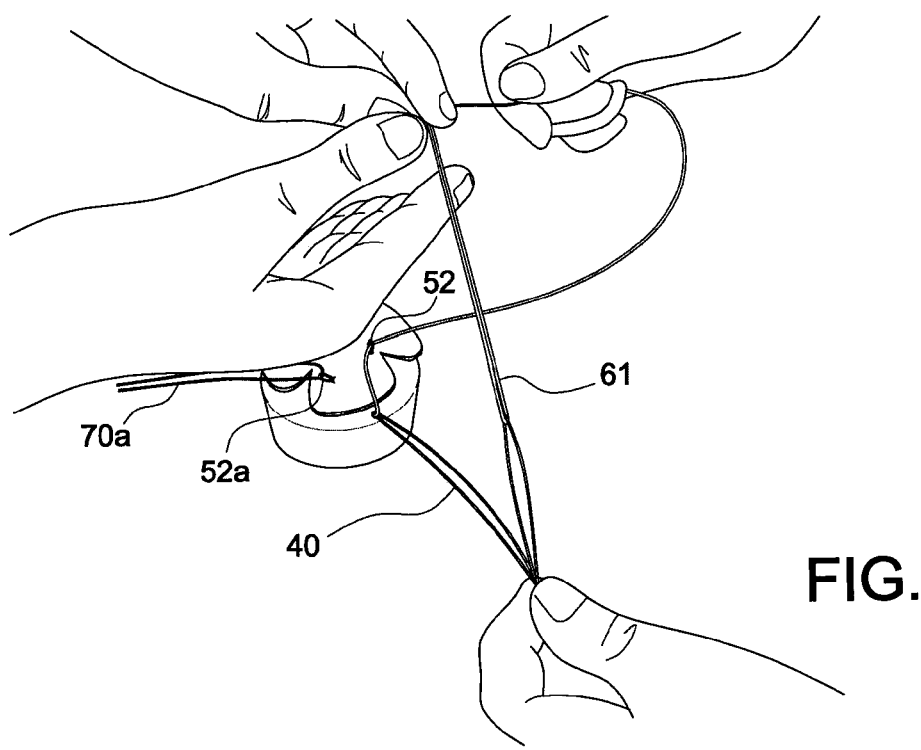

FIG. 14 (step 14)—Fold the end so it can be shuttled through the anchor 60.

Figure 15:
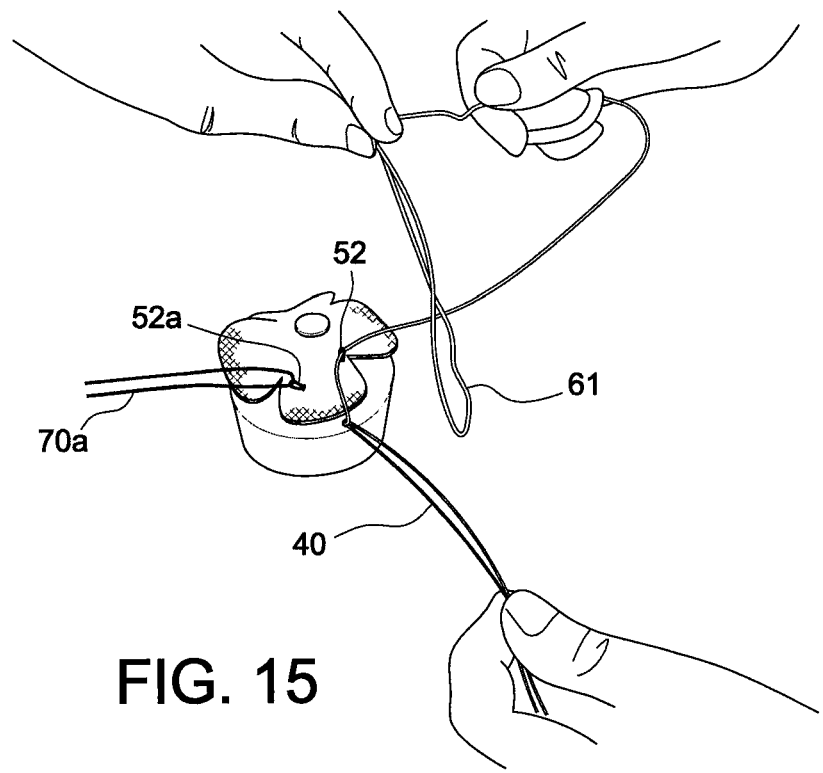

FIG. 15 (step 15)—Alternate view of step 14.

Figure 16:
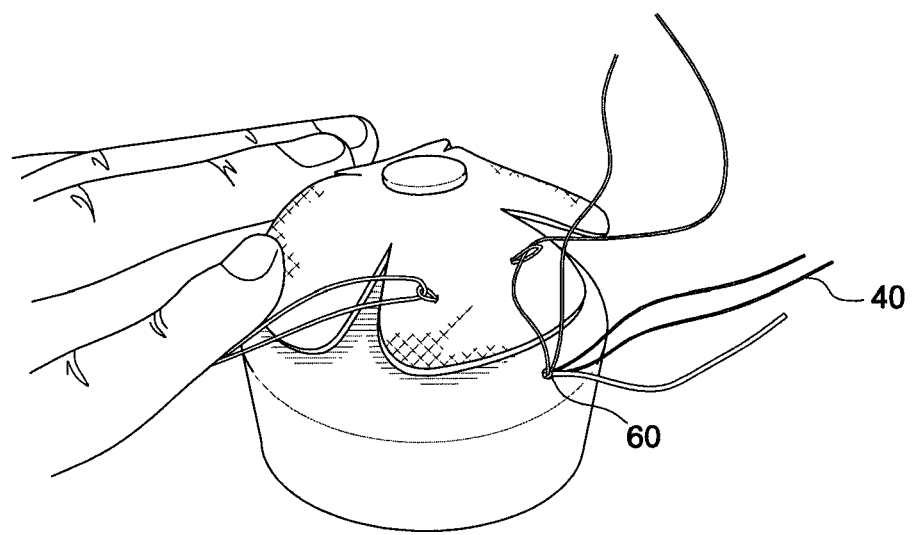
Figure 17:
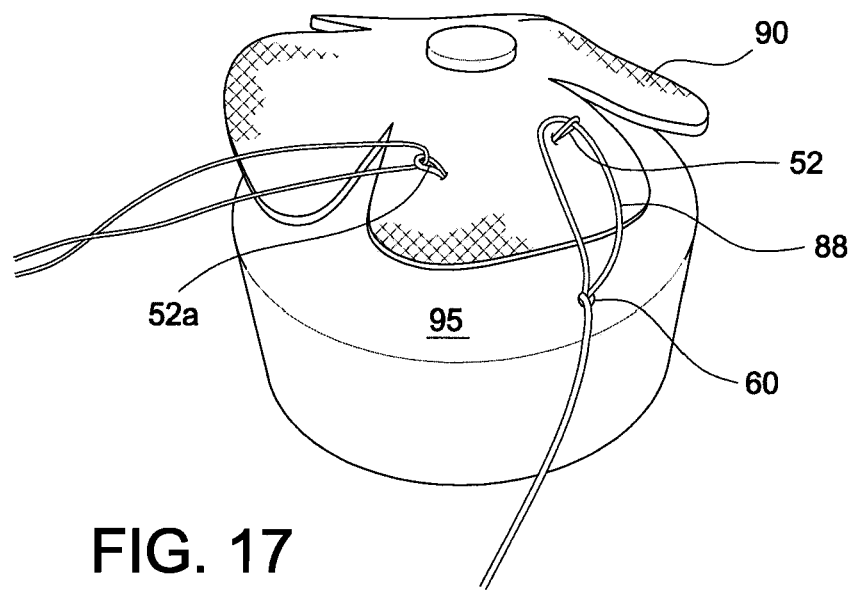

FIG. 16 (step 16)—Pull nitinol wire 40 so the suture 61 is fed through a splice 66 thereof (FIG. 23) on the anchor 60, creating a tensionable suture loop 88 with a non-fixed adjustable perimeter (FIG. 17). The internals of anchor 60 are of similar design to the knotless SutureTak® anchor.

FIG. 17 (step 17)—Pull the slack of the suture 61 until proper tension is desired. Tension can be delayed until final anchor 60 is inserted and suture is loaded.

Figure 18:
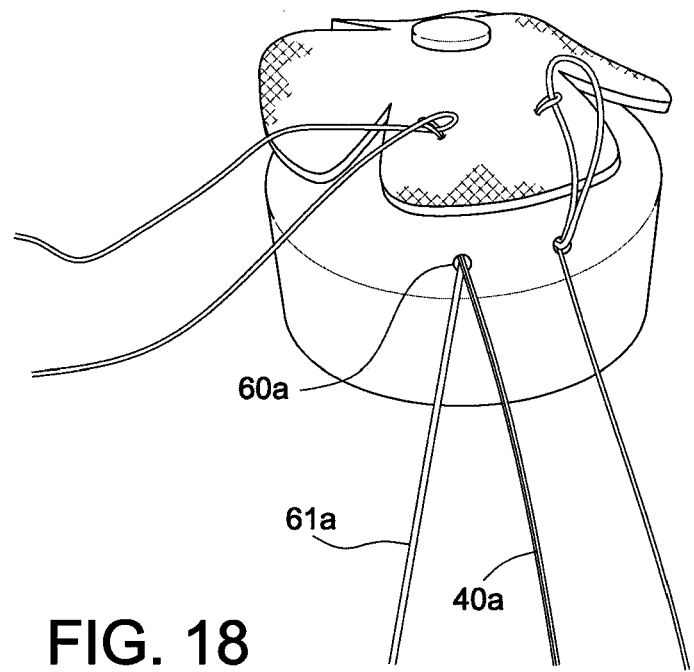

FIG. 18 (step 18)—Insert second lateral row anchor 60a with suture 61a and shuttle/pull device 40a (suture passing device 40a or nitinol loop 40a).

Figure 19:
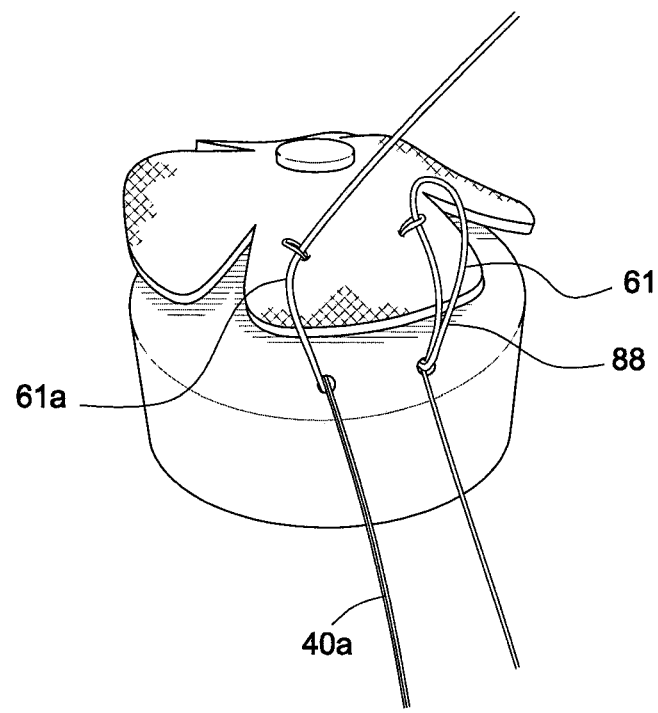

FIG. 19 (step 19)—In same manner as steps 7-12, feed the lateral row suture 61a through the other medial row anchor 50a.

Figure 20:
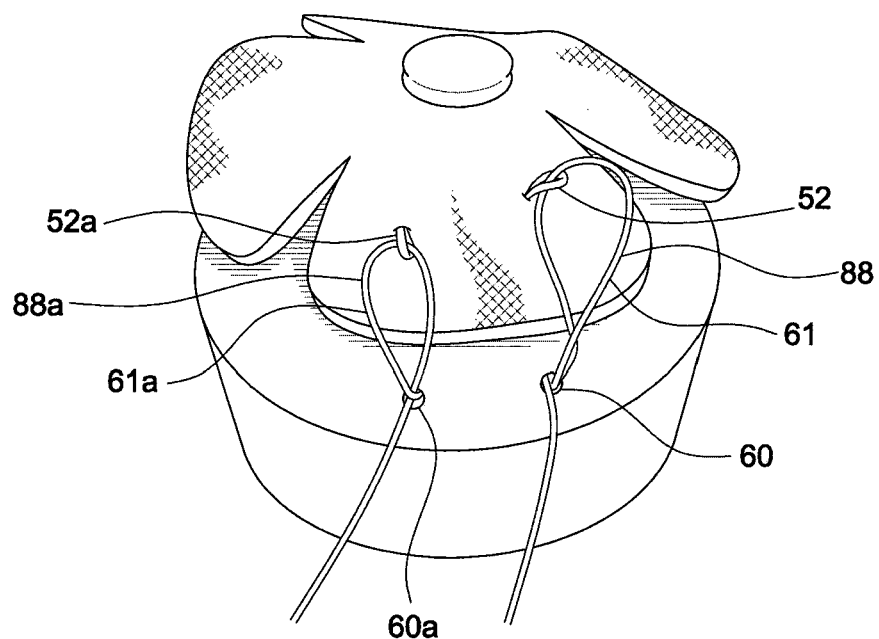

FIG. 20 (step 20)—In the same manner as steps 13-16, feed the suture 61a through the splice 66 of the lateral row anchor 60a to form self-cinching, knotless tensionable loop 88a (with a non-fixed adjustable perimeter), and pull out the slack.

Figure 21:
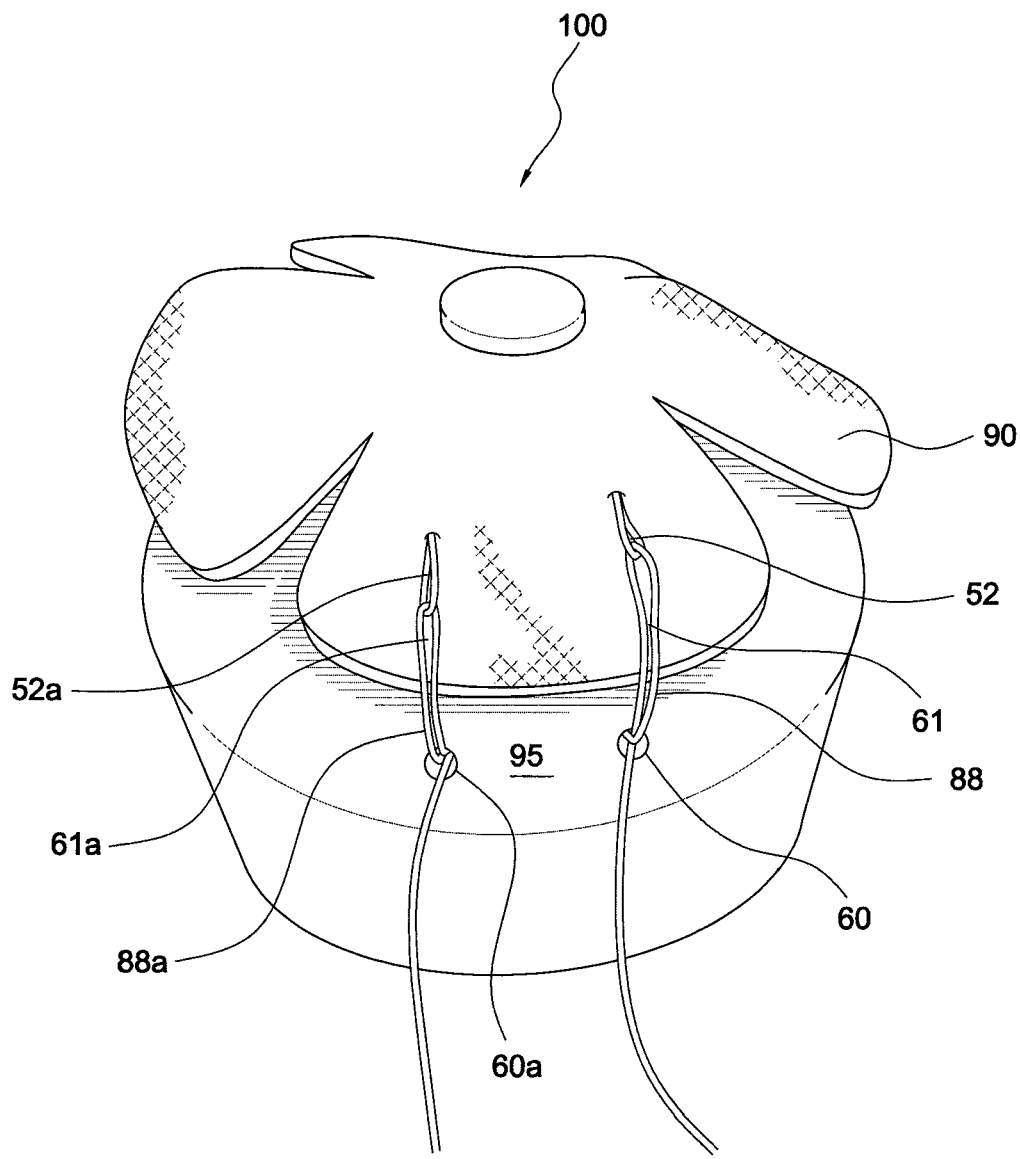

FIG. 21 (step 21)—Pull both strands to desired tension and trim free ends of suture. The final construct (tissue repair) 100 is provided with a first suture loop 52, 52a and a second suture loop 88, 88a that are interconnected.

The exemplary steps above may be conducted with a plurality of medial anchors (such as exemplary anchors 50, 50a) and a plurality of lateral anchors (such as exemplary anchors 60, 60a) depending on the characteristics of the tissue repair.

Alternate embodiments: Medial anchors can be reversed to form an "X" pattern instead of two vertical lines. Lateral row anchors can contain two sutures with two nitinol loaders each to create an "X" pattern in addition to the one shown in the picture.

The SutureTak® suture anchors 60, 60a are available in a variety of sizes, materials and suture options. The BioComposite anchor options contain a molded-in suture to reinforce the strength of the anchor and suture eyelet. The PEEK SutureTak® is a nonabsorbable suture anchor with a material eyelet which provides superior abrasion resistance due to PEEK's low coefficient of friction. The SutureTak® implant system simplifies anchor insertion using a guide to prepare a pilot hole precisely on the glenoid rim. The drill is removed and the implant is inserted through the same guide, creating a simple reproducible technique.

Each of the lateral knotless SutureTak® anchors 60, 60a may be preferably a self-cinching knotless construct which is pre-loaded with a tensionable construct formed of suture attached to a shuttling device (shuttle/pull device or suture passing device (for example, a FiberLink™ or a nitinol loop)). To assemble the lateral self-cinching knotless anchor 60, 60a, a suture (which is typically braided or multifilament is preloaded) onto the anchor body by tying a static knot. Prior to the fastening of the anchor to the driver, the suture passing device (for example, a FiberLink™ or a nitinol loop) is threaded through suture (i.e., attached to the suture through a splice region located outside or inside the anchor body). The suture passing device includes an eyelet/loop for passing suture and, optionally, a pull-ring. The tensionable knotless anchor is loaded with the tensionable construct formed of suture attached to the suture passing device.

As detailed above, once the anchor 60, 60a is implanted into bone, the suture 61, 61a is passed over the tissue 90 which is to be reattached to bone 95 and also through the fixed loop 52, 52a (fixed eyelet 52, 52a) of medial anchor 50, 50a. Suture 61, 61a is subsequently passed through eyelet/loop of the suture passing device 40. Suture passing device 40 is then pulled, thereby pulling suture towards tensionable knotless anchor so that it doubles on itself outside the body of the tensionable knotless anchor but within the bone hole/socket/tunnel (as detailed above) and forms a splice.

The splice mechanism may be located within the anchor or outside the anchor but within the drill hole/socket, so that the final splice construct will be contained within the bone but not within the anchor body.

The surgical repairs of the present invention may employ any type of flexible material or suture 61, 61a, for example FiberWire® or FiberTape® or FiberChain®. In another embodiment, any combination of suture, suture tape, and/or suture chain may be employed, depending on the characteristics of the specific surgical repair and/or as desired.

Flexible strand or cord 61, 61a may be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strand 61, 61a may be also in the form of flat suture tape (for example, a collagen stuffed suture tape or a high strength suture tape, such as disclosed in U.S. Pat. No. 7,892,256) or a combination of suture and tape, a stiff material, or combination of stiff and flexible materials, depending on the intended application. The flexible strand 61, 61a may be also in the form of a suture chain described in U.S. Pat. No. 7,803,173 and/or in U.S. Pat. No. 7,981,140, the disclosures of both of which are incorporated by reference in their entirety. The strands 61, 61a may also be formed of a stiff material, or combination of stiff and flexible materials, depending on the intended application. The strands may be also coated and/or provided in different colors.

The lateral knotless suture constructs 60, 60a of the repair systems detailed below use a mechanism similar to that of knotless anchors detailed and described in U.S. Patent Application Publication Nos. 2013/0096611 and 2013/0165972, the disclosures of both of which are incorporated by reference in their entirety herein.

The methods of the present invention allow for multi-anchor tissue repair without the need for tying knots but still having the ability to tension the tissue properly, after anchor implantation.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A surgical assembly for tissue repair, comprising:
   a first fixation device comprising a first body and a fixed first loop with a fixed perimeter attached to the first body; and
   a second fixation device comprising a second body, a longitudinal axis, a proximal end and a distal end, and a tensionable construct pre-loaded on the second fixation device, the tensionable construct consisting of a flexible strand, the flexible strand having a splice through itself thereby forming an adjustable second loop having an adjustable perimeter, wherein the splice is located within the second body and extends between the proximal end and the distal end,
   wherein the flexible strand is attached to the fixed first loop and extends between the first fixation device and the second fixation device, and over at least a portion of tissue to be repaired, and
   wherein at least a portion of the first fixation device and at least a portion of a second fixation devices are located in bone.

2. The surgical assembly of claim 1, wherein the tensionable construct is a self-locking construct.

3. The surgical assembly of claim 1, wherein the second fixation device is a knotless, adjustable, self-locking anchor.

4. The surgical assembly of claim 1, wherein a shuttling device is attached to the flexible strand, and the shuttling device is a suture passing instrument or a wire loop.

5. The surgical assembly of claim 1, wherein the second body has a plurality of outer ridges.

6. The surgical assembly of claim 1, wherein the first fixation device is a swivel anchor provided with a tip that has a shaft and an eyelet attached to the shaft, and a separate cannulated fixation device, wherein the tip is rotatable relative to the cannulated fixation device and is configured to swivel relative to the cannulated fixation device, the eyelet being pre-loaded with a flexible strand that forms the fixed first loop.

7. The surgical assembly of claim 6, wherein, when the swivel anchor is anchored into a socket of a bone, the cannulated fixation device is configured to be advanced over the shaft so that the cannulated fixation device advances over the shaft of the tip of the swivel anchor and engages and fully seats the tip and the eyelet pre-loaded with the flexible strand and forms the first loop extending out of the swivel anchor and over a surface of the bone.

8. A tissue repair system for attachment of tissue to bone, comprising:
   a first tensionable suture construct extending between a first plurality of fixation devices, the first tensionable suture construct including an adjustable suture loop of a first fixation device of the first plurality of fixation devices; a fixed suture loop of a second fixation device of the first plurality of fixation devices attached to the adjustable suture loop; and a splice located within a body of the second fixation device of the first plurality of fixation devices,
   wherein at least a portion of the first fixation device and at least a portion of a second fixation devices are located in bone.

9. The tissue repair system of claim 8, wherein the first adjustable suture loop and the fixed suture loop are interconnected.

10. The tissue repair system of claim 8, wherein at least a portion of the adjustable suture loop and at least a portion of the fixed suture loop extend above tissue and above bone.

11. The tissue repair system of claim 8, wherein the adjustable suture loop is attached to an open distal end of the first fixation device of the first plurality of fixation devices.

12. The tissue repair system of claim 8, wherein the second fixation device of the first plurality of fixation devices is a push-in anchor, a swivel anchor or a screw-in anchor.

13. The tissue repair system of claim 8, wherein the first fixation device of the first plurality of fixation devices is a SutureTak® anchor.

14. The tissue repair system of claim 8 further comprising a second tensionable suture construct extending between a second plurality of fixation devices, the second tensionable suture construct including an adjustable second suture loop of a first fixation device of the second plurality of fixation devices; a fixed second suture loop of a second fixation device of the second plurality of fixation devices attached to the adjustable second suture loop; and a splice located within a body of the second fixation device of the second plurality of fixation devices, wherein the adjustable second suture loop and the fixed second suture loop are interconnected.

15. The tissue repair system of claim 8 wherein the repair is a knotless double row rotator cuff repair.

* * * * *